United States Patent
Younis et al.

(10) Patent No.: US 11,903,944 B1
(45) Date of Patent: Feb. 20, 2024

(54) EXPERIMENTAL MODEL USING PAZOPANIB-INDUCED CARDIOTOXICITY

(71) Applicant: KING FAISAL UNIVERSITY, Al-Ahsa (SA)

(72) Inventors: Nancy Safwat Younis, Al-Ahsa (SA); Maged Elsayed Mohamed, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/203,378

(22) Filed: May 30, 2023

(51) Int. Cl.
*A61K 31/506* (2006.01)
*A61K 9/00* (2006.01)

(52) U.S. Cl.
CPC .......... *A61K 31/506* (2013.01); *A61K 9/0019* (2013.01)

(58) Field of Classification Search
CPC .................................................... A61K 31/506
See application file for complete search history.

(56) References Cited

U.S. PATENT DOCUMENTS

| | | |
|---|---|---|
| 11,028,448 B2 | 6/2021 | Innocenti et al. |
| 2021/0052549 A1 | 2/2021 | Petitjean et al. |
| 2022/0133684 A1 | 5/2022 | Armstrong et al. |

OTHER PUBLICATIONS

Kempton et al., Clinical and Experimental Hypertension, 2018, 40(6): 524-533.*
Hou et al., Journal of Cancer Research and Clinical Oncology, 2021, 147: 2407-2420.*
Kempton, A., et al., "Pazopanib for Renal Cell Carcinoma Leads to Elevated Mean Arterial Pressures in a Murine Model," Clin. Exp. Hypertens., 40(6): pp. 524-533 (2018).
Akman, T., et al., "Prevention of Pazopanib-Induced Prolonged Cardiac Repolarization and Proarrhythmic Effects," Arq. Bras. Cardiol. 103(5): pp. 403-409 (2014).
French, K.J. et al., "Differences in Effects on Myocardium and Mitochondria by Angiogenic Inhibitors Suggest Separate Mechanisms of Cardiotoxicity," Toxicology Pathology 38(5): pp. 691-702 (2010).
Cooper, S. L., et al., "Long-term cardiovascular effects of vandetanib and pazopanib in normotensive rats," Pharmacol. res. Perspect. 7(3): e00477 (2019).
Pinto, T. M. et al., "Lessons from rat models of hypertension: from Goldblatt to genetic engineering," Cardiovascular Research 39: pp. 77-88 (1998).

* cited by examiner

*Primary Examiner* — Rei Tsang Shiao
(74) *Attorney, Agent, or Firm* — Nath, Goldberg & Meyer; Richard C. Litman

(57) ABSTRACT

An experimental model using pazopanib-induced cardiotoxicity is provided. The experimental model using pazopanib-induced cardiotoxicity includes administering an effective dosing regimen of pazopanib to induce a cardiotoxicity in a subject. The induced cardiotoxicity may include hypertension, arrhythmia, or cardiac toxicity. The dosing regimen may include administering a single dose or administering one or more daily doses of pazopanib. The dosing regiment may continue for a period of time between at least 10 and at least 30 days. The dose of pazopanib may be between 25 and 350 mg/kg.

19 Claims, 7 Drawing Sheets

EXPERIMENTAL MODEL USING PAZOPANIB-INDUCED CARDIOTOXICITY

INCORPORATION BY REFERENCE OF MATERIAL SUBMITTED IN COMPUTER-READABLE FORM

The Applicant hereby incorporates by reference the sequence listing contained in the XML file titled 33102.96U.xml, created Apr. 30, 2023, and having 7,718 bytes of data.

BACKGROUND

1. Field

The disclosure of the present patent application relates to methods of establishing experimental models of cardiotoxicity, and particularly to an experimental model using pazopanib-induced cardiotoxicity.

2. Description of the Related Art

In general, models are developed to mimic aspects of biological processes or diseases found in animals or humans. Animal models are selected to be sufficiently like humans in their anatomy, physiology, or response to a pathogen to allow researchers to extrapolate the results of animal model studies to better understand human physiology and disease. The use of animal models allows researchers to perform experiments that would be impractical or impossible to conduct with humans. However, animal models are only approximations of the actual human response, and there are numerous examples throughout history where animal models have failed to predict specific drug interactions discovered when testing reached humans.

Cardiotoxicity remains a significant side effect of many chemotherapy drugs, and thus there is a significant demand to develop new cardioprotective agents. The development of cardioprotective agents, in turn, is constrained by the need to develop new and reliable models of cardiotoxicity.

Thus, an experimental model using pazopanib-induced cardiotoxicity solving the aforementioned problems is desired.

SUMMARY

The experimental model using pazopanib-induced cardiotoxicity includes administering an effective dosing regimen of pazopanib to induce cardiotoxicity in a subject. In certain embodiments, the induced cardiotoxicity may include hypertension, arrhythmia, or cardiac toxicity. In certain embodiments, the dosing regimen may include administering a single dose or administering one or more daily doses of pazopanib. In certain embodiments, the dosing regimen may continue for a period of time between at least about 10 and at least about 30 days. Further, the dose of pazopanib may be between about 25 and about 350 mg/kg.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
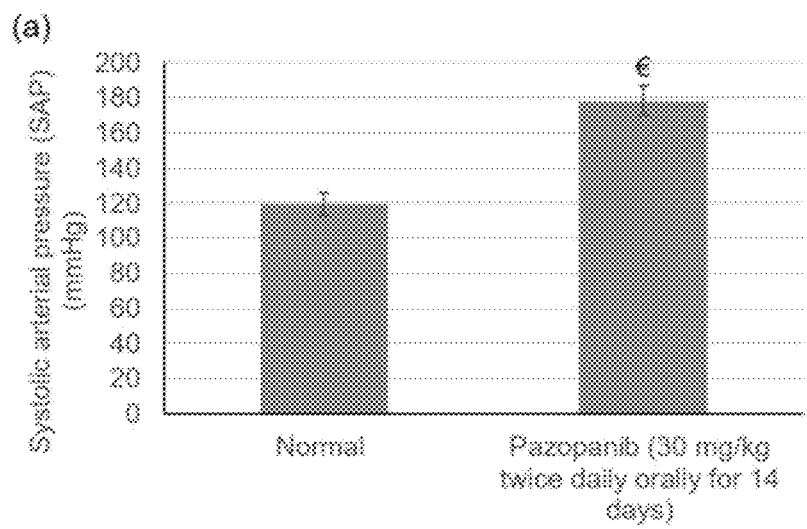
FIGS. 1(A)-1(C) depict bar graphs illustrating the effects of Pazopanib 30 mg/kg administration twice daily orally for 14 days on blood pressure indices including (FIG. 1A) systolic arterial pressure (SAP), (FIG. 1B) diastolic arterial pressure (DAP), and (FIG. 1C) mean arterial pressure (MAP).

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The pazopanib or pharmaceutical compositions thereof can be administered to a subject by any suitable route. For example, the compositions can be administered orally (including buccally and sublingually), and/or parenterally. As used herein, "parenteral" administration refers to modes of administration other than through the gastrointestinal tract, which includes, by way of non-limiting example, intravenous, intramuscular, intraperitoneal, subcutaneous and infusion.

As used herein, "subject" may refer to any mammal, including but not limited to animals frequently used as animal models of human diseases, such as mice, rats, rabbits, pigs, or monkeys.

As used herein, "cardiotoxicity" refers to the occurrence of heart dysfunction in the form of either electric or muscle damage, which may result in heart toxicity. Cardiotoxicity may cause the heart to become weaker and/or loose efficiency in pumping blood. Examples of cardiotoxicity may include arrhythmias, hypertension, or cardiac toxicity.

As used herein, "arrhythmia" refers to an irregular heartbeat that occurs when the electrical signals that coordinate the heart's beats don't work properly. The faulty signalling can result in the heart beating too fast (tachycardia), too slow (bradycardia), or irregularly.

As used herein, "hypertension" refers to high blood pressure, a long-term medical condition in which the blood pressure in the arteries is persistently elevated. High blood pressure generally refers to an adult having blood pressure that is persistently above 130/80 or 140/90 mmHg.

As used herein, "cardiac toxicity" refers to the toxicity or death of heart muscle cells, causing muscle damage.

The experimental model using pazopanib-induced cardiotoxicity includes administering an effective dosing regimen of pazopanib to induce cardiotoxicity in a subject. In certain embodiments, the induced cardiotoxicity may include by way of non-limiting example hypertension, arrhythmia, cardiac toxicity, or any combination thereof. In certain embodiments, the dosing regimen may include administering a single dose or administering one or more daily doses of pazopanib. In certain embodiments, the dosing regimen may continue for a period of time between at least about 10 and at least about 30 days. Further, the dose of pazopanib may be between about 25 and about 350 mg/kg.

In some embodiments, the subject may be selected from animal species commonly used to model human disease, including but not limited to mice, rats, rabbits, pigs, and monkeys.

Pazopanib is a potent multi-targeted tyrosine kinase inhibitor (TKI), targeting many cellular biomarkers such as VEGFr, PDGFr, and c-kit; thus, pazopanib is commonly used as an anticancer agent. Pazopanib has the chemical formula $C_{21}H_{23}N_7O_2S$, and the structure:

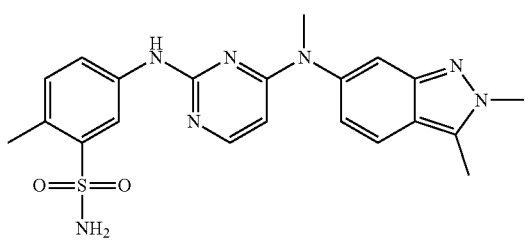

Pazopanib sometimes induces cardiotoxicity as a side effect during treatment. This drug-induced cardiotoxicity may be characterized by cardiac arrhythmia (QT prolongation), heart muscle damage (cardiomyopathy), hypertension, or congestive heart failure. Thus, Pazopanib was identified as a candidate for developing in vivo animal models of cardiotixicty.

In an embodiment, the experiment model may include inducing hypertension by administering between about 25 mg/kg pazopanib and about 35 mg/kg pazopanib twice daily. The route of administration may be oral administration, and the administration may continue for a period of between about 10 and about 20 days. In a particular embodiment, the experimental model may include inducing hypertension by orally administering about 30 mg/kg pazopanib twice daily for about 14 days.

In an embodiment, the experiment model may include inducing arrhythmia by administering between about 75 mg/kg pazopanib and about 125 mg/kg pazopanib daily. The route of administration may be oral administration, and the administration may include administering a single dose over a period of between about 1 and about 5 hours. In a particular embodiment, the experimental model may include inducing arrhythmia by orally administering about 100 mg/kg pazopanib in a single dose administered over a period of about 3 hours.

In an embodiment, the experiment model may include inducing cardiac toxicity by administering between about 250 mg/kg pazopanib and about 350 mg/kg pazopanib daily. The route of administration may be oral administration, and the administration may continue for a period of between about 15 and about 30 days. In a particular embodiment, the experimental model may include inducing hypertension by orally administering about 300 mg/kg/day pazopanib daily for about 21 days.

In an embodiment, the experiment model may include inducing cardiac toxicity by administering between about 25 mg/kg pazopanib and about 35 mg/kg pazopanib daily. The route of administration may be i.p. administration, and the administration may continue for a period of between about 15 and about 30 days. In a particular embodiment, the experimental model may include inducing hypertension by i.p. administering about 30 mg/kg/day pazopanib daily for about 21 days.

The experimental model using pazopanib-induced cardiotoxicity may be better understood in view of the following examples.

Example 1

Use of the Experimental Model Using Pazopanib-Induced Cardiotixicty to Elucidate the Role of Toll-like Receptors in Pazopanib Cardiotoxic Side Effects This experimental protocol was permitted by the Institutional Animal Care and Use Committee of King Faisal University. All the experiments were executed in harmony with the relevant procedures and regulations of the Ethical Conduct for the Use of Animals in Research at King Faisal University. Male Sprague Dawley rats weighing 150-200 g were purchased and accommodated in polypropylene cages and upheld at 27±2° C. under a 12 h light/dark sequence. Rats were kept and observed for 1 week in the animal house. The animals were fed with standard rat feed and allowed water ad libitum.

Protocol

Animals were distributed into 5 groups, each group containing 6 rats (n=6). Group 1 is the control group in which animals were injected with normal saline intraperitoneally (IP). Group 2: The animals were treated with Pazopanib 30 mg/kg twice daily orally for 14 days to induce hypertension. This group represents the "Experimental animal model for hypertension." Group 3: The animals were treated with Pazopanib 100 mg/kg orally as a single dose. This group represents the "Experimental animal model for arrhythmia." Group 4: The animals were treated with Pazopanib 300 mg/kg/day orally for 21 days. This group represents the "Experimental animal model for Cardiac toxicity (oral)" Group 5: The animals were treated with Pazopanib 21 mg/kg/day intraperitoneally (IP) for 30 days. This group represents the "Experimental animal model for Cardiac toxicity (IP)"

Electrocardiogram (ECG) Recording and Measurement for Arrhythmia Identification

At the end of the experiments, urethane-anaesthetized rats (1.5 g/kg) were placed in a prone position on a board, and an ECG was continuously recorded using noninvasive computerized ECG apparatus from Kent Scientific (Torrington, CT, USA). Heart rate, ST segment, P wave, QT, P-R and R-R intervals, and QRS complex were calculated from ECG recordings electronically.

Blood Pressure (BP) Recording and Measurement

Blood pressure measurements were performed using a noninvasive computerized tail-cuff system from Emka Technologies' Systems (Paris, France), which involved placing a cuff on the animal's tail to occlude the blood flow. The pressure was raised and then slowly released. The cuff pressure when the pulse signal reappears is intended as the systolic pressure. The cuff pressure when the pulse signal level recovers its initial level is intended to be the diastolic pressure.

Cardiac Toxicity Identification

Blood samples were collected, and centrifuged (10 min/ 4000 rpm) to separate serum which was then stored in a −80° C. for biochemical analysis. Thereafter, the anaesthetized animals were sacrificed, and the hearts of different investigational groups were separated, and stored in a −80° C. for subsequent biochemical parameters determination.

ELISA kits, following the manufacturer's instructions, were used to measure serum cardiac marker levels of CPK, CK-MB, cTnT, cTnI and LDH.

Determination of the Involvement of Toll-Like-Receptors (TLRs) in all Animal Models Total RNA was extracted from the cardiac tissue samples according to the Trizol kit instructions. The MMLV-RT kit was used to reverse transcribe total RNA into cDNA. The TLR4 primer (5'-AGTGTATCGGTGGTCAGTGTGCT-3' (SEQ ID NO: 1), 3'-AAACTCCAGCCACACATTCC-5' (SEQ ID NO: 2)), TLR2 (5'-AAACTGTGTTCGTGCTTTCTGA-3' (SEQ ID NO: 3), 3'-CTTTCTTCTCAATGGGTTCCAG-5' (SEQ ID NO: 4)), MYD88 (5'-GAGATCCGCGAGTTTGAGAC-3' (SEQ ID NO: 5), 3'-CTGTTTCTGCTGGTTGCGTA-5' (SEQ ID NO: 6)) were used to detect and quantify related genes in the cDNA using Real-time quantitative PCR. In a 25 μL reaction volume, PCR was performed as follows: initial denaturation for 4 min at 94° C., followed by denaturation for 30 s at 94° C., annealing for 30 s at 62° C., and extension for 2 min at 72° C. for 35 cycles, and final extension for 10 min at 72° C. qPCR was applied using SYBR ExScript RT-PCR kit, and quantification examinations were accomplished via an Opticon-2 Real-time PCR reactor (MJ Research, Capital Court, Reno, NV, USA). qPCR results were obtained using Step PE Applied Biosystems (Waltham, MA, USA) software. Relative gene expression data were calculated using the (2-ΔΔCq2) method and presented as a fold change. Target gene expressions were assessed and related to the internal reference β-actin gene using the primer (5'-ATCCTGCGTCTGGACCTGG-3' (SEQ ID NO: 7), 5'-TTGGCATAGAGGTCTTTACGGAT-3' (SEQ ID NO: 8)), and the results were presented in the figures as relative expressions.

Statistical Analysis

Data were expressed as mean±standard error of the mean (SEM) for six animals (n=6) in each group. Statistically significant differences between the groups were determined using one-way ANOVA followed by Tukey's test as a post-hoc analysis. In all cases, probability values of p<0.05 were taken as statistically significant.

Pazopanib induced high blood pressure in the animal model.

Figure 1B:
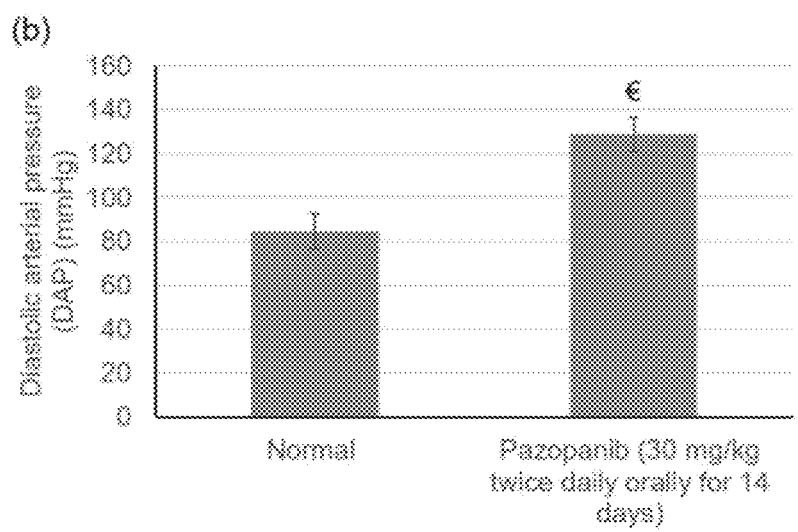
Figure 1C:
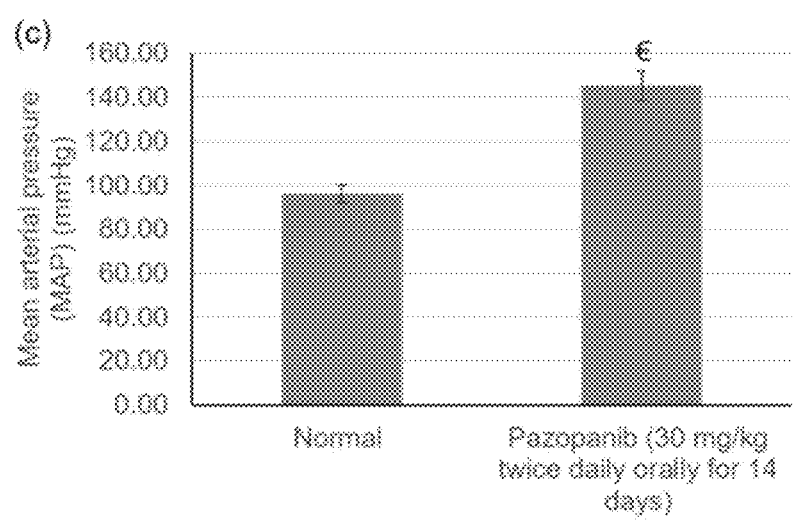
Figure 2A:
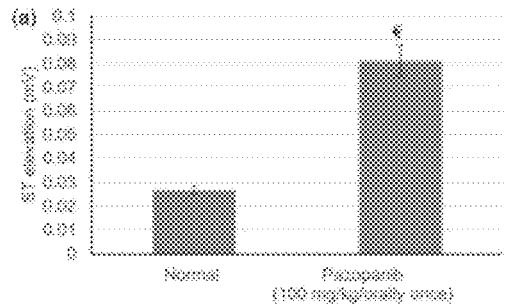
FIGS. 2(A)-2(F) depict bar graphs illustrating the effects of Pazopanib 100 mg/kg orally as a single dose to induce arrhythmia after 3 hours on ECG parameters including p wave duration, QRS complex duration, QT interval, ST-segment amplitude, RR interval duration and PR interval duration. Values were expressed as mean±SEM (n=6). € indicates statistically significant from the normal group, ($p<0.05$) using one-way ANOVA followed by Tukey's test as a post-hoc analysis.
Figure 2B:
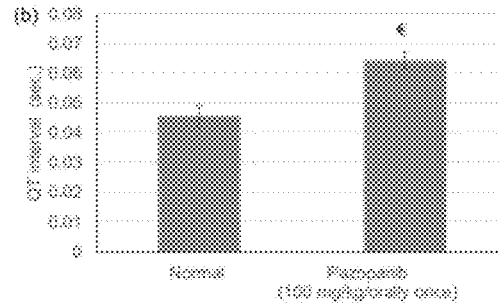
Figure 2C:
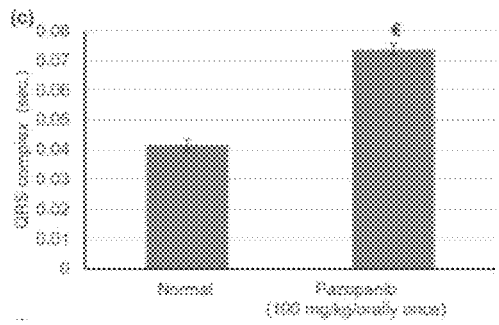
Figure 2D:
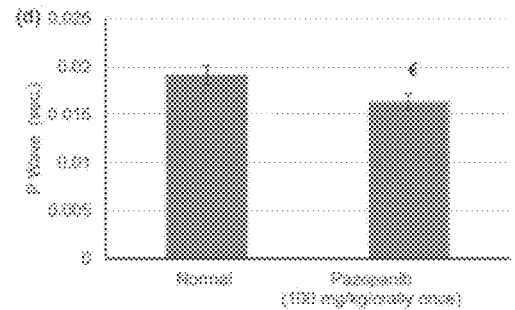
Figure 2E:
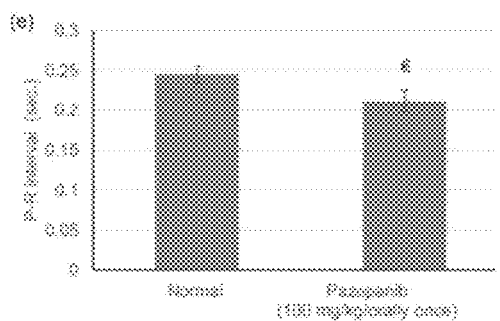
Figure 2F:
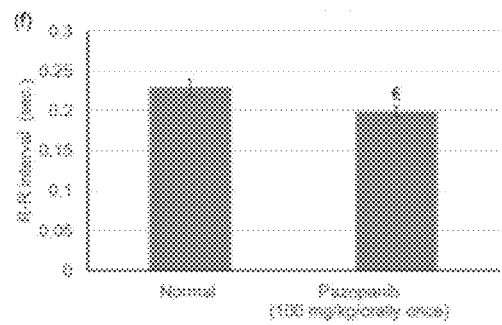
Figure 3A:
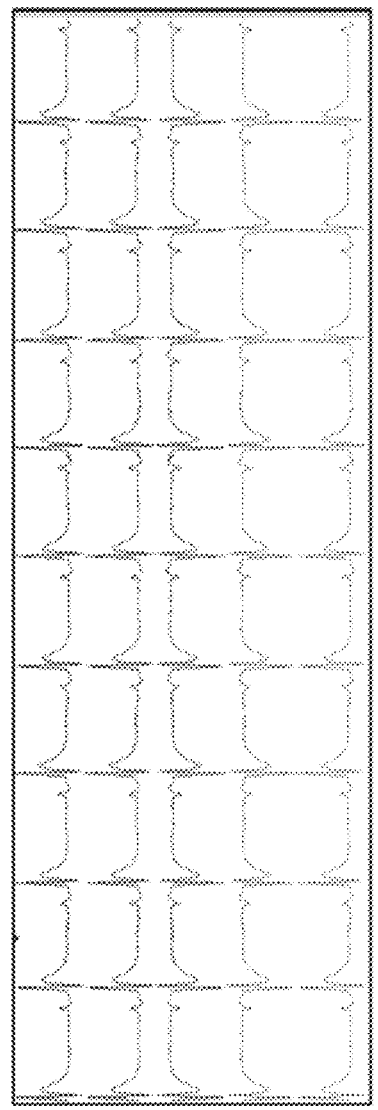
FIGS. 3(A)-3(B) depict computerized electrocardiogram (ECG) traces for normal animals (FIG. 3(A)) and showing the effects of Pazopanib 100 mg/kg administered orally as a single dose to induce arrhythmia after 3 hours (FIG. 3(B)).
Figure 3B:
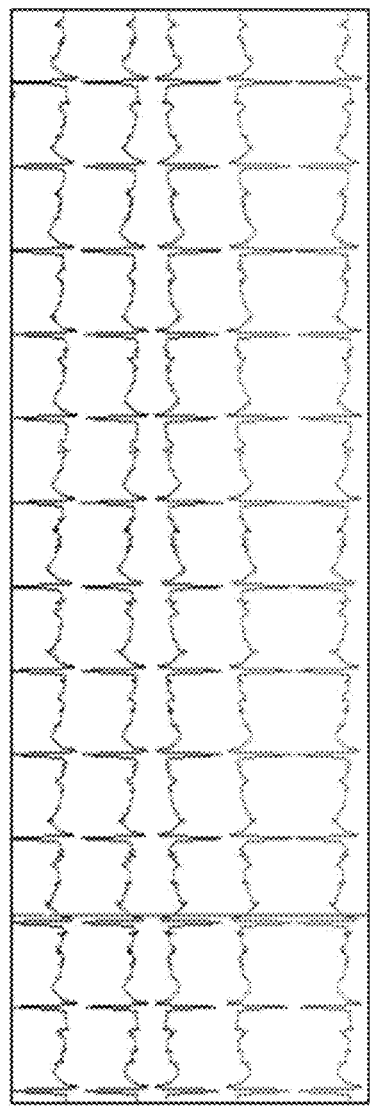
Figure 4A:
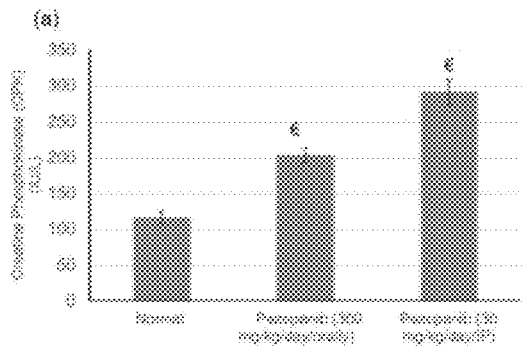
FIGS. 4(A)-4(E) depict bar graphs illustrating the effect of administration of Pazopanib 300 mg/kg/day orally and 30 mg/kg/day intraperitoneally (IP) for 21 days on numerous cardiac indicator enzymes, including creatine phosphokinase (CPK), creatine kinase-myocardial bound (CK-MB), cardiac troponin T (cTnT), cardiac troponin I (cTnI) and lactate dehydrogenase (LDH). Values were expressed as mean±SEM (n=6). € indicates statistically significant from the normal group, ($p<0.05$) using one-way ANOVA followed by Tukey's test as a post-hoc analysis.
Figure 4B:
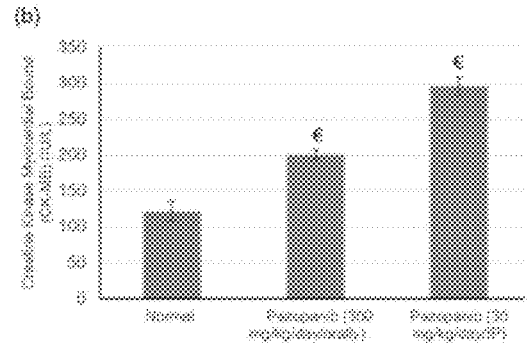
Figure 4C:
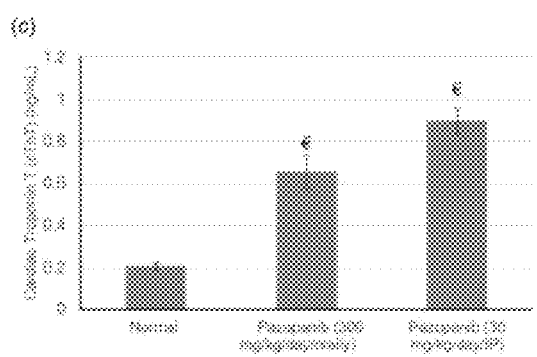
Figure 4D:
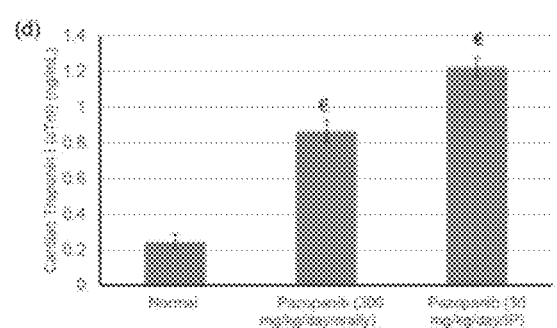
Figure 4E:
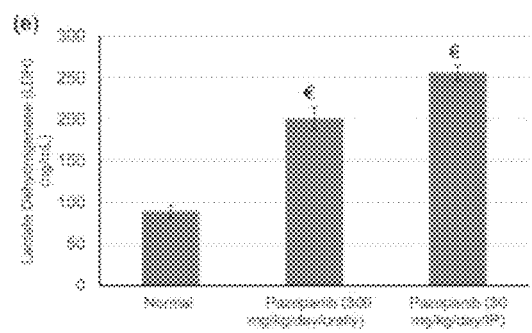

All the pressure indices, including systolic blood pressure, diastolic blood pressure and mean blood pressure, were elevated in group 2 when compared to normal animals, as shown in FIG. 1(A)-FIG. 1(C). Group 2 are the animals that were treated with Pazopanib 30 mg/kg twice daily orally for 14 days to induce hypertension. This group represented the "Experimental animal model for hypertension".

Pazopanib as an arrhythmia-inducing drug in animal models

In group 3, the animals were treated with Pazopanib 100 mg/kg orally as a single dose to induce arrhythmia after 3 hours. This group represented the "Experimental animal model for arrhythmia."

The ECG parameters, including p wave duration, QRS complex duration, QT interval, ST-segment amplitude, RR interval duration and PR interval duration, are displayed in FIGS. 2(A)-2(F) and FIGS. 3(A)-3(B). The acquired results displayed substantial variations in the ECG of Pazopanib-administered rats, including a significant (p<0.05) prolongation of QT and QRS intervals, and ST segment amplitude compared to the control. In addition, Pazopanib administration resulted in the shortening of the p wave, P-R, and R-R intervals. Both actions, the prolongation of QT, QRS intervals, and ST elevation and the limitation of the p wave, P-R, and R-R intervals reveal diverse cardiac arrhythmias and conduction abnormalities associated with Pazopanib administration.

Pazopanib-Induced Cardiac Toxicity in Animal Models

The effects of Pazopanib 300 mg/kg/day orally and 30 mg/kg/day intraperitoneally (IP) for 21 days on numerous cardiac enzymes (creatine phosphokinase (CPK), creatine kinase-myocardial bound (CK-MB), cardiac troponin T (cTnT), cardiac troponin I (cTnI) and lactate dehydrogenase (LDH)) are shown in FIGS. 4(A)-4(E). Pazopanib significantly (p<0.05) augmented cardiac enzymes (CPK, CK-MB, cTnT, cTnI and LDH) as compared with normal rats indicating the presence of cardiac toxicity as a side effect for the drug.

Effects of Pazopanib on TLR4 Gene Expression Levels in all Animal Models

Figure 5:
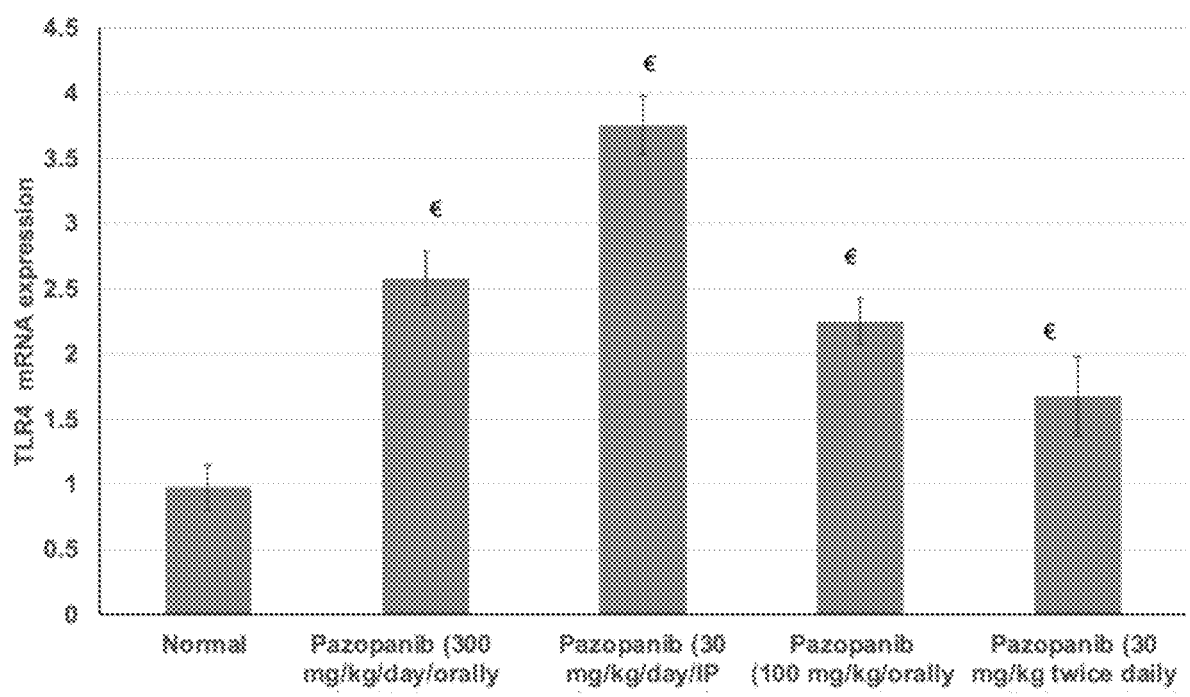
FIG. 5 depicts a bar graph illustrating the effects of Pazopanib administration in different regimens on TLR4 gene expression levels. Values were expressed as mean±SEM (n=6). € indicates statistically significant from the normal group, ($p<0.05$) using one-way ANOVA followed by Tukey's test as a post-hoc analysis.

Experimental animal model for hypertension (Pazopanib 30 mg/kg twice daily orally for 14 days), for arrhythmia (Pazopanib 100 mg/kg orally as a single dose), and for cardiotoxicity (Pazopanib 300 mg/kg/day orally and 30 mg/kg/day intraperitoneally (IP) administration for 30 days) exhibited significantly increased Toll-Like Receptors 4 (TLR4) gene expressions, as shown in FIG. 5.

It is to be understood that the experimental model using pazopanib-induced cardiotoxicity is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of inducing an experimental animal model of cardiotoxicity in a subject by significantly increasing Toll-Like Receptors 4 (TLR4) gene expression in the subject comprising administering an effective dosing regimen of pazopanib.

2. The method of inducing cardiotoxicity of claim 1, wherein the subject is a rat.

3. The method of inducing cardiotoxicity of claim 1, wherein the cardiotoxicity comprises hypertension.

4. The method of inducing cardiotoxicity of claim 3, comprising administering between about 25 mg/kg pazopanib and about 35 mg/kg pazopanib twice daily to the subject for a period of between about 10 and about 20 days.

5. The method of inducing cardiotoxicity of claim 4, wherein the administering of the pazopanib is oral administration.

6. The method of inducing cardiotoxicity of claim 4, comprising administering about 30 mg/kg pazopanib twice daily for about 14 days.

7. The method of inducing cardiotoxicity of claim 1, wherein the cardiotoxicity comprises arrhythmia.

8. The method of inducing cardiotoxicity of claim 7, comprising administering between about 75 mg/kg pazopanib and about 125 mg/kg pazopanib to the subject.

9. The method of inducing cardiotoxicity of claim 8, wherein the administering of the pazopanib is oral administration.

10. The method of inducing cardiotoxicity of claim 8, comprising administering the pazopanib to the subject over a period of between about 1 and about 5 hours.

11. The method of inducing cardiotoxicity of claim 10, comprising administering about 100 mg/kg pazopanib to the subject over a period of about 3 hours.

12. The method of inducing cardiotoxicity of claim 1, wherein the cardiotoxicity comprises cardiac toxicity.

13. The method of inducing cardiotoxicity of claim 12, comprising administering pazopanib daily to the subject for a period of between about 15 and about 30 days.

14. The method of inducing cardiotoxicity of claim 13, comprising administering pazopanib daily to the subject for a period of about 21 days.

15. The method of inducing cardiotoxicity of claim 12, wherein the administering of the pazopanib is oral administration.

16. The method of inducing cardiotoxicity of claim 15, comprising administering between about 250 mg/kg pazopanib and about 350 mg/kg pazopanib to the subject.

17. The method of inducing cardiotoxicity of claim 16, comprising administering about 300 mg/kg pazopanib to the subject.

18. The method of inducing cardiotoxicity of claim 12, wherein the administering of the pazopanib is intraperitoneal administration.

19. The method of inducing cardiotoxicity of claim 18, comprising administering between about 25 mg/kg pazopanib and about 35 mg/kg pazopanib to the subject.

* * * * *